United States Patent [19]
Yamaoka et al.

[11] Patent Number: 5,772,439
[45] Date of Patent: Jun. 30, 1998

[54] HYBRID DENTAL IMPLANT

[75] Inventors: Akira Yamaoka, Osaka; Kazuaki Nishimura, Sakai; Tomomi Nakanishi, Osaka; Naho Michie, Sakai, all of Japan

[73] Assignee: Kanebo Limited, Tokyo, Japan

[21] Appl. No.: 624,871

[22] Filed: Mar. 27, 1996

[30] Foreign Application Priority Data

Mar. 28, 1995 [JP] Japan .................................... 7-096215

[51] Int. Cl.⁶ .................................................. A61C 8/00
[52] U.S. Cl. ........................................ 433/201.1; 433/173
[58] Field of Search ................................... 433/172, 173, 433/174, 175, 176, 201.1; 523/115, 114

[56] References Cited

U.S. PATENT DOCUMENTS

| | | | |
|---|---|---|---|
| 5,071,351 | 12/1991 | Green, Jr. et al. | 433/174 |
| 5,439,951 | 8/1995 | Glimcher et al. | 523/115 |
| 5,501,706 | 3/1996 | Arenberg | 433/201.1 |
| 5,584,880 | 12/1996 | Martinez | 433/201.1 |

FOREIGN PATENT DOCUMENTS

| | | |
|---|---|---|
| 0128706-A3 | 12/1984 | European Pat. Off. . |
| 0256695-A3 | 2/1988 | European Pat. Off. . |
| 0693523-A2 | 1/1996 | European Pat. Off. . |
| 6-7381 | 1/1994 | Japan . |
| 7-330531 | 12/1995 | Japan . |
| WO 89/1247 | 12/1989 | WIPO . |
| WO 90/13302 | 11/1990 | WIPO . |

OTHER PUBLICATIONS

Kojima, "Material Report R & D, Application of Carbon Fiber/Carbon Composites to Biomaterial," *Kino Zairyo*, 33–40, (1988).

U.S. application No. 08/615,233, filed Mar. 15, 1996.

Hanes et al., "Cell and Fiber Attachment to Demineralized Cementum from Normal Root Surfaces," *J.Periodontol,:* 60.4 (1989).

*Primary Examiner*—Cary E. O'Connor
*Attorney, Agent, or Firm*—Hamilton, Brook, Smith & Reynolds, P.C.

[57] ABSTRACT

The hybrid dental implant of this invention has cementum particle on a surface of a dental implant substrate.

16 Claims, 1 Drawing Sheet

HYBRID DENTAL IMPLANT

BACKGROUND OF THE INVENTION

1. Field of the Invention

The present invention relates to a dental implant, and more specific ally to a hybrid dental implant which induces an alveolar bone-periodontal membrane-dental root attachment system similar to the attachment system of an alveolar bone-periodontal membrane-dental root of a normal, natural tooth.

2. Description of the Related Art

Today, as we progress toward an aged society, there arises a problem that, while the life expectancy of human beings is being prolonged due to recent advancements in medical technology and the fulfillment of social welfare, the life of human tooth is not similarly prolonged. Restoration of teeth having the normal occlusive function, which is indispensable for sustaining comfortable eating, in now eagerly desired by elderly people and those who have lost a large number of teeth.

Conventionally, prosthesis such as dentures has been generally employed for treating a patient who has lost a large number of teeth. However, the denture forms a gap between the denture and the gingiva, and overloads the other remaining teeth. Thus, there are problems that the patient having the denture cannot bite and chew foods effectively and that the remaining teeth may be injured prematurely.

In recent years, in order to restore the occlusive function, a treatment as shown in FIG. 2 has been clinically applied. In this treatment, a dental implant 2 made of a biocompatible material such as titanium and hydroxyapatite is inserted into an alveolar bone 5 through a gingiva 3, and an upper structure 4 such as an artificial tooth is mounted on the dental implant 2. Such a dental implant, however, forms a periodontium which is different from the original tissue structure, causing dental ankylosis where the alveolar bone comes into direct contact with the dental implant. As a result, the periodontium transmits the occlusive pressure directly to the jawbone, causing a destruction of the alveolar bone as a subsequent reaction against mechanical stress, and the dental implant itself is oscillated or sinks in the alveolar bone. Moreover, once the periodontium around the dental implant has an infectious disease or inflammation due to accumulation of dental plaque and the like on the root, such a disease or inflammation rapidly spreads to the alveolar bona. Due to these problems, rapid and wide spread use of the dental implant has been prevented. Thus, the largest drawback of the conventional dental implant known to date is that the attachment of the dental implant to the periodontium in different from the inherent attachment system.

In the inherent attachment system, the cementum and the periodontal membrane exist between the dental root and the alveolar bone, and a bundle of collagen fibers run vertically from the dental root toward the alveolar bona. The bundle of collagen fibers serves to tightly bind the dental root to the alveolar bone. The cementum not only serves to bond the dental root and the periodontal membrane, but also plays an important role of maintaining the periodontium balanced for a longer period of time. The periodontal membrane functions by buffering the occlusive pressure, perceiving the occlusive pressure via a baroreceptor, and a nervous adjusting function or a reflex function based on the perception. The periodontal membrane also serves as a barrier against an infectious disease and inhibits induction of osteoolasts which cause bone absorption.

Thus, the construction of periodontium having the inherent attachment system is necessary for successful functioning of the dental implant, and it in therefore desired to provide a dental implant capable of constructing such an periodontium.

Japanese Laid-open Patent Publication No. 6-7381 disclosed a method for constructing a pseudo-periodontal membrane around a dental implant. According to this method, periodontal membrane cells collected from an extracted tooth are cultured, and the cultured periodontal membrane cells are further subjected to an enrichment culture to form a pseudo-periodontal membrane. The pseudo-periodontal membrane is interposed between the dental implant and the alveolar bone or jawbone. In this method, however, it is required to use periodontal membrane cells obtained from the recipient himself or herself who is to receive the prosthesis treatment or periodontal membrane cells obtained from others which are not rejected by the recipient. This method is therefore not suitable for general use. Further, the procedure required to produce the pseudo-periodontal membrane by culture and the process for implanting the dental implant are complicated. Moreover, it is difficult to maintain the pseudo-periodontal membrane stably for a long period. Due to these problems, clinical practice of this method is difficult.

An experiment using a monkey is reported where a dental implant made of vitreous carbon (FRS implant) was implanted into the portion where the lower jawbone molar tooth had been extracted (A. Kojima, "Application of carbon fiber/carbon composite as biological material", Kino Zairyo, 1033-40, 1988). The monkey was sacrificed two years after the implantation to observe the periodontium formed around the dental implant. The report describes that connective tissue made of collagen fibers corresponding to the periodontal membrane of a normal tooth was observed. However, such a connecting tissue made of collagen fibers was only partially formed. Moreover, this observation result was obtained after a period as long an two years had passed. In consideration of these facts, this method is too disadvantageous to be clinically applied immediately.

SUMMARY OF THE INVENTION

The hybrid dental implant of this invention has cementum particles on a surface of a dental implant substrate.

In one embodiment of the invention, a bioabsorbable membrane containing the cementum particles is formed on the dental implant substrate.

In another embodiment of the invention, the surface of the dental implant substrate is made of hydroxyapatite.

In still another embodiment of the invention, the bioabsorbable membrane is made of at least one material selected from the group consisting of gelatin, crosslinked gelatin, collagen, and crosslinked collagen.

In still another embodiment of the invention, the hybrid dental implant is sterilized with ethylene oxide gas.

In still another embodiment of the invention, the hybrid dental implant is sterilized with electron beams.

Thus, the invention described herein makes possible the advantage of providing a hybrid dental implant which is free from dental ankylosis caused by direct contact with the alveolar bone and induces an alveolar bone-periodontal membrane-dental root attachment system similar to the attachment system of an alveolar bone-periodontal membrane-dental root of a normal tooth.

These and other advantages of the present invention will become apparent to those skilled in the art upon reading and understanding the following detailed description with reference to the accompanying figures.

DESCRIPTION OF THE PREFERRED EMBODIMENTS

Figure 2:
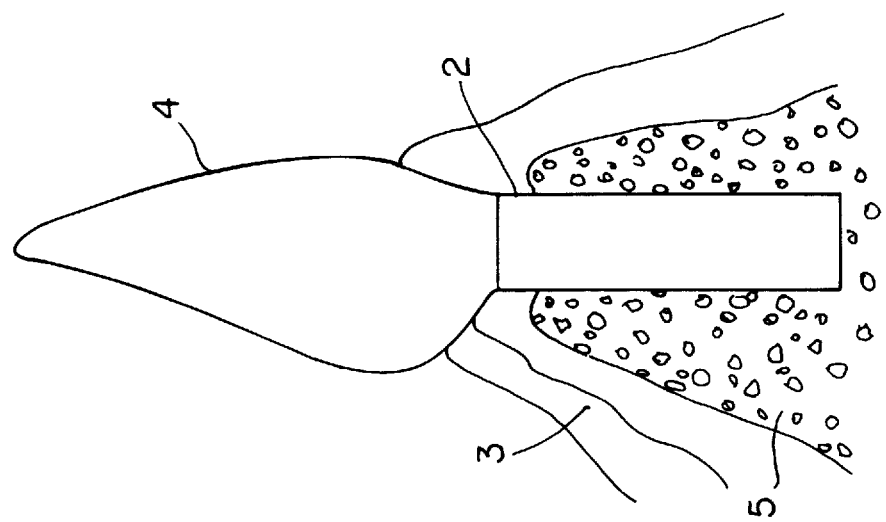
FIG. 2 is a schematic sectional view of a periodontium formed around a conventional dental implant inserted into an alveolar bone.

The hybrid dental implant according to the present invention includes cementum particles on the surface of a dental implant substrate.

The material for the dental implant substrate used in the present invention is not limited, but can be any material generally used for a typical dental implant. Especially used is a material which in less harmful to organisms and excellent in toughness and friction resistance. The preferred example of the dental implant substrate in at least one material selected from the group of titanium, hydroxyapatite, silica, alumina, zirconia, and bioglass. In particular, hydroxyapatite, which is a highly biocompatible material, is more preferred.

The cementum particles used in the present invention are prepared from mat yellowish white cementum having a Mohs' hardness of about 4 to about 5, a specific gravity of about 2.02 to about 2.04, and a refractive index of about 1.562 to about 1.566. The cementum is a bone-like hard tissue having a thickness of about 0.02 to about 0.5 mm covering the dental root surface of animals higher than reptiles. The cementum doom not contain blood vessels inside and is generally distinguishable from the bone. The cementum is classified into the primary cementum (acellular cementum) and cellular cementum. In particular, the primary cementum and cellular cementum of higher mammals such as cows and pigs are preferred. The primary cementum is more preferred.

The shape of the cementum particles used in the present invention is not limited, but any shape such as a granular shape may be used. Also, the cementum particles used in the present invention are preferably microparticles. When the cementum microparticles are immobilized to the surface of the dental implant substrata, the area of the immobilized cementum becomes a large surface area so that the dissolution and absorption of the cementum are improved. Thus, periodontal tissue is more easily induced around the dental implant. In the present invention, the average diameter of the cementum particles (i.e., average of the lengths along the major axis of the cementum particles) is preferably about 0.001 to about 0.1 mm, and more preferably about 0.001 to about 0.075 mm. Such cementum particles that satisfy the above range requirement of the average diameter are mostly absorbed into the tissue of the organism before the formation of a periodontium around the dental implant.

The cementum particles are prepared by using appropriate means, for example, scraping the dental root surface of an extracted tooth with a dental scaler, and then grinding the scraped pieces of cementum with a mortar, a ball mill, and the like.

The amount of cementum particles applied to the surface of the dental implant substrate varies depending on the shape, particle size distribution, and physiological activity of the cementum used. The amount of the cementum particles is preferably about 0.1 to about 6.0 mg per cm$^2$ of the surface of the dental implant substrate. More preferred is about 0.5 to about 4.0 mg in order to facilitate formation of a periodontium.

The method for applying and immobilizing the cementum particles to the surface of the dental implant substrate is not limited, but any conventional method can be employed. For example, the cementum particles may be adhered and/or immobilized to the surface of the dental implant substrate by use of an immobilizer. An organic or inorganic compound capable of immobilizing the cementum particles to the surface of the dental implant substrate may be used as the immobilizer.

Alternatively, a bioabsorbable membrane containing the cementum particles may be attached to the surface of the dental implant substrate.

Examples of the organic compound used as the immobilizer include synthetic polymers and natural polymers, both including bioabsorbable polymers. In particular, bioabsorbable polymers are preferred an they are less harmful to organisms, facilitate dissolution and absorption of cementum particles into the tissue to the organism, and serve in forming a periodontium of the dental implant similar to that of a normal, natural tooth.

Examples of the bioabsorbable polymers include; aliphatic polyesters such as polylactic acid, polyglycolic acid, and poly($\epsilon$-caprolactone); proteins and polysaccharides such as collagen, gelatin, albumin, dextran, chitin, chitosan, and fibrin; and crosslinked structures thereof. In particular, at least one bioabsorbable polymer selected from the group consisting of gelatin, crosslinked gelatin, collagen, and crosslinked collagen is preferably used.

The method for immobilizing the cementum particles to the surface of the dental implant substrate with the above organic compounds as an immobilizer is not limited, but conventional methods for immobilizing a particulate substance to a substrate surface can be employed. For example, when gelatin in used an the immobilizer, the immobilization is performed in either of the following manners.

(1) A crosslinking agent such an glycerol polyglycidyl ether in added to an aqueous gelatin solution and dissolved. The resultant solution is applied to the surface of the dental implant substrate, and an appropriate amount of cementum particles are dispersed on the surface applied with the solution. The resultant surface of the dental implant substrate is then lyophilized.

(2) A crosslinking agent such as glycerol polyglycidyl ether is added to a gelatin solution and dissolved. An appropriate amount of cementum particles are dispersed in the solution. The resultant suspension is then applied to the surface of the dental implant substrate, or the dental implant substrate is immersed in the suspension. Then, the resultant surface of the dental implant substrate is lyophilized.

Thus, the cementum particles are immobilized to the surface of the dental implant substrate. The concentration of the gelatin solution used in the above method is preferably in the range of about 20 to about 500 g/l, and the amount of the crosslinking agent is preferably in the range of about 0.2 to about 50 g/l.

Examples of the inorganic compound used as the immobilizer include hydroxyapatite, silica, alumina, zirconia, and calcium oxide. In particular, hydroxyapatite which in a component existing in the organism is most preferable.

The method for immobilizing the cementum particles to the surface of the dental implant substrate with the above inorganic compounds au an immobilizer is not limited, but conventional methods for immobilizing a particulate substance to a substrate surface can be employed. For example, when hydroxyapatite is used as the immobilizer, the immobilization is performed in the following manner. Powdered hydroxyapatite is suspended in water and sufficiently agitated to form a slurry. An appropriate amount of the cementum particles is dispersed in the slurry, and the dental implant substrate in immersed in the slurry. After removal from the slurry, the surface of the dental implant substrate is lyophilized.

Thus, the cementum particles are immobilized to the surface of the dental implant substrate. In this method, the amount of hydroxyapatite is preferably in the range of about 200 to about 800 g/l. The above method using inorganic compounds may further include the step of adding the aforementioned bioabsorbable polymer such as gelatin to the suspension for enhancing the immobilization of the cementum particles to the surface of the dental implant substrate, and/or the step of coating the immobilized cementum particles with the aforementioned bioabsorbable polymer such as gelatin for preventing the immobilized cementum particles from separating from the substrate.

The method for attaching the bioabsorbable membrane with cementum particles immobilized therein to the surface of the dental implant substrate will now be described. The bioabsorbable membrane may be made of any material which can dissolve and/or decompose to be absorbed into the tissue of the organism when the resultant hybrid dental implant is inserted in the alveolar bone. Examples of the material for the bioabsorbable membrane include the aforementioned bioabsorbable polymers. In particular, at least one material selected from the group consisting of gelatin, crosslinked gelatin, collagen, and crosslinked collagen which have high biocompatibility or bioaffinity is preferably used.

The structure of the bioabsorbable membrane is not limited, but a porous structure is preferable to increase the efficiency of dissolution and/or absorption of the membrane into the tissue of the organism.

The method for producing the bioabsorbable membrane with cementum particles immobilized therein is not limited, but conventional methods for producing a membrane with a particulate substance immobilized therein can be employed. For example, such a bioabsorbable membrane is produced in the following manner. A crosslinking agent such as glycerol polyglycidyl ether is dissolved in an aqueous gelatin solution. The resultant solution is poured to spread on a smooth plate and cooled (at 5° to 10° C. for 20 minutes, for example) to obtain membrane-like gelatin gal. The gelatin gel is then lyophilized to remove water and heated (at 110° C. for two hours, for example) to obtain a crosslinked gelatin membrane with a porous structure. Thereafter, a suspension obtained by dispersing an appropriate amount of cementum particles in a gelatin solution with the same concentration as that of the aqueous gelatin solution used for dissolving the crosslinking agent is applied to the surface of the crosslinked gelatin membrane. The resultant membrane in then lyophilized. Thus, the bioabsorbable membrane with cementum particles immobilized inside and/or to the surface of the membrane in produced. In this method, the concentration of the gelatin solution is preferably in the range of about 10 to about 200 g/l, and the amount of the crosslinking agent is preferably in the range of about 0.1 to about 20 g/l.

The thus produced bioabsorbable membrane is attached to the surface of the dental implant substrate by a known method. For example, an aqueous gelatin solution with a crosslinking agent such as glycerol polyglycidyl other dissolved therein is applied to the surface of the dental implant substrate. The bioabsorbable membrane obtained by the above method is then attached to the resultant surface of the dental implant substrate. By drying the membrane, the membrane containing the cementum particles is immobilized to the surface of the dental implant substrate. In this method, the concentration of the gelatin solution applied to the surface of the dental implant is preferably in the range of about 10 to about 200 g/l, and the amount of the crosslinking agent is preferably in the range of about 0.1 to about 20 g/l.

Thus, the hybrid dental implant according to the present invention is obtained by applying and immobilizing the cementum particles to the surface of the dental implant substrate. The hybrid dental implant is generally sterilized before clinical use. Examples of the method for sterilizing the dental Implant include ethylene oxide gas sterilization, electron beam sterilization, and radiation sterilization. In particular, in order to ensure that the cementum particles continue to be immobilized to the surface of the dental implant substrate, either one of the ethylene oxide gas sterilization and the electron beam sterilization is preferably used. In the radiation sterilization, an attachment system similar to the periodontium of a normal tooth may not be obtained according to the sterilization conditions. These sterilizing methods are known to those skilled in the art.

Figure 1:
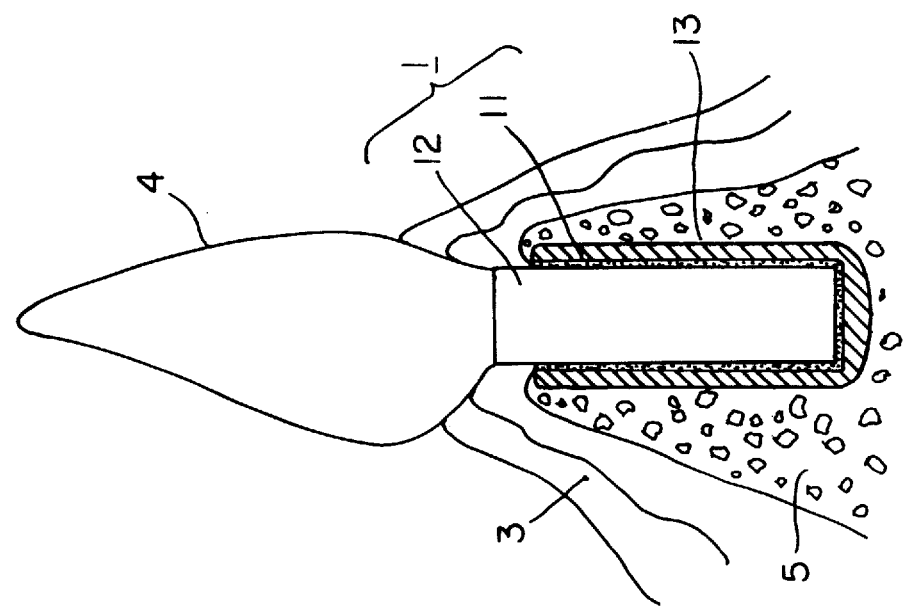
FIG. 1 is a schematic sectional view of a periodontium formed around a hybrid dental implant according to the present invention inserted in an alveolar bone.

FIG. 1 shows an example of the hybrid dental implant of the present invention obtained by the methods described above. Referring to FIG. 1, a hybrid dental implant 1 includes cementum particles 11 immobilized to the surface of dental implant substrate 12. The hybrid dental implant 1 is inserted into an alveolar bone 5 located inside a gingiva 3 by a known method, so as to allow an upper structure 4 such as an artificial dental tooth to be mounted on the hybrid dental implant 1. A periodontal membrane 13 composed of a fibrous connective tissue is then formed between the hybrid dental implant 1 and the alveolar bone 5. The hybrid dental implant according to the present invention in suitable as a dental implant for elderly people and those who have loot a number of teeth.

EXAMPLES

The present invention will now be described by way of examples, though it is not restricted to these examples.

PRODUCTION EXAMPLE 1

Preparation of bovine cementum particles

Teeth were extracted from a bovine jawbone, supplied from a slaughterhouse, with dental extracting forceps and stored frozen at −4° C. After thawing, attached gingiva tissue was immediately removed by use of a surgical knife and a surgical scaler. At that time, the cellular cementum were scraped off. After these procedures, curettage of the primary cementum was performed, 100 to 200 strokes per tooth, using a surgical scaler. Since the thickness of the bovine primary cementum was 0.4 to 0.5 mm, the curettage corresponding to this number of strokes did not allow the scaler to reach the dentin underlying the cementum. By the above method, 2.3 g of abraded primary cementum pieces were obtained from 40 bovine teeth. The primary cementum was collected in a 25 ml tube containing physiological saline, and centrifuged. After the supernatant solution was removed, the abraded primary cementum pieces precipitated on the bottom of the tube were collected, dried spontaneously on a clean bench, and then lyophilized. The dried abraded pieces were placed in a mortar, pulverized with a pestle, and sifted to obtain bovine cementum, particles with a diameter of about 0.075 mm or less. The average diameter of the bovine cementum particles was about 0.014 mm.

PRODUCTION EXAMPLE 2

Preparation of crosslinked gelatin membrane

To an aqueous solution (viscosity: 28 millipoise, jelly toughness: 96 g (6.66%)) containing 5% by weight of commercially available gelatin (Nippi Inc.,) was added 3 parts by weight (to 100 parts by weight of gelatin) of glycerol polyglycidyl ether (Nagase Chemicals Ltd.) as a crosslinking agent and dissolved. Two grams of the solution was poured to spread on a polymethylmethacrylate plate (size: 10 cm×10 cm, thickness: 2 mm) framed on one side with a Teflon® adhesive tape with a width of 1 cm and a thickness of 0.6 mm. The plate was mounted on a horizontal support kept at 5° to 10° C., so that the solution was cooled for 20 minutes to allow gelation. The plate was then mounted on a support kept at −70° C. to allow the gelated solution to be frozen by cooling from its lower side. The resulting frozen gel was then lyophilized at a temperature not higher than 25° C., thereby to obtain a gelatin membrane. The thus-obtained gelatin membrane was heated at 110° C. for two hours for crosslinking. After the heating, the membrane was washed with distilled water at 50° C., removing residual uncrosslinked gelatin and the crosslinking agent, and lyophilized again, to obtain the crosslinked gelatin membrane. The thus-obtained crosslinked gelatin membrane was a double-layer porous membrane including a solid layer on one side and a layer with a number of pores on the other side. The size of the membrane was 8 cm×8 cm, the average thickness thereof was 0.18 mm, and the average pore diameter was 0.093 mm.

PRODUCTION EXAMPLE 3

Preparation of crosslinked gelatin membrane with bovine cementum particles immobilized therein To 1 ml of an aqueous solution (viscosity: 28 millipoise, jelly toughness: 96 g (6.66%)) containing 0.2% by weight of commercially available gelatin (Nippi Inc.) was added 61.44 mg of the bovine cementum particles obtained in Production Example 1 to obtain a suspension. The crosslinked gelatin membrane obtained in Production Example 2 was placed on a polymethylmethacrylate plate with the solid side of the membrane facing the plate, and the above suspension was poured to spread on the side of the membrane, having pores. The amount of the bovine cementum particles applied to the crosslinked gelatin membrane was 0.96 mg per $cm^2$ of the membrane. The resultant crosslinked gelatin membrane was placed in a sealed vessel and left to stand for one minute while the pressure in the vessel is lowered to 30 mmHg. The pressure was then returned to the ambient pressure. After repeating this process three times, the gelatin membrane was left to stand for 30 minutes under the ambient pressure. The above-mentioned process allows the bovine cementum particles to deposit on the membrane. The membrane was lyophilized with a lyophilization apparatus (FTS-FD-6-54B, FTS Systems, Inc.) to obtain the crosslinked gelatin membrane with bovine cementum particles immobilized therein.

EXAMPLE 1

Preparation and experimentation of hybrid dental implant with bovine cementum particles immobilized thereto An aqueous solution (viscosity 28 millipoise, jelly toughness 96 g (6.66%) containing 2% by weight of commercially available gelatin (Nippi Inc.) was thinly applied to a commercially available dental implant substrate having a surface made of hydroxyapatite (Apaceram, length: 9 mm, inner diameter: 4.5 mm, Asahi Optical Co., Ltd.) with a small brush. The crosslinked gelatin membrane with bovine cementum particles immobilized therein obtained in Production Example 3 was cut into an appropriate size, and attached to the surface of the dental implant substrate so that no overlap of the membrane nor a portion uncovered with the membrane would be formed on the surface. The resultant substrate was lyophilized with a lyophilization apparatus (FTS-FD-6-54B, FTS Systems, Inc.) to obtain the hybrid dental implant with bovine cementum particles immobilized thereon. The resultant hybrid dental implant was placed in a polyethylene bag and sealed. The bag was than irradiated with light from an ultraviolet sterilizing lamp (15 Watt, Toshiba Corp.) placed 30 cm apart from the bag for 30 minutes each from the upper and lower sides of the bag. Then, the bag was stored in a refrigerator at 5° C.

Two healthy Japanese monkeys having full dentitions and weighing approximately 10 kg, wore used. In order to prepare for the dental implant placement, the right and left maxillary and mandibular premolars and the first molar were extracted. Three months after the extraction, a full thickness mucoperiosteal flap was elevated after making remote vestibular incisions in order to expos alveolar rests. Thereafter, using a dental implant implanting kit, the above hybrid dental implant was implanted in experimentally created edentulous ridges. Then, the gingival flap was repositioned, followed by suture.

The Japanese monkey was sacrificed 12 weeks after implantation of the dental implants, tissues were immediately fixed via perfusion of half-strength Karnousky fixative. Block specimens including the dental implant and the corresponding peri-implant soft and hard tissues were then removed and placed in 2.5% glutaraldehyde-2.0% paraformaldehyde fixative (pH 7.2, 4° C.) for 2 weeks. After fixation, experimental areas were cut with the Exakt-Cutting-Grinding System (EXAKT, Hamburg, Germany) in the bucco-lingual direction to produce specimens. All specimens were dehydrated in an ascending series of alcohols and embedded in Technovit 7200 methacrylate resin (Kalzer, Wehrheim, Germany). After polymerization, blocks were sectioned at 200 $\mu$m according to the above-mentioned Exakt-Cutting-Grinding System and subsequently ground to a thinness of 70 to 80 $\mu$m. Sections were stained with hematoxylin-eosin prior to histological analysis.

The alveolar bone and the dental implant were found separated by a certain distance and a soft tissue membrane consistent with perioumtal ligament-like tissue was formed in the entire area between the alveolar bone and the dental implant. Cementoblastic cells deeply stained with hematoxylin were formed on the entire interface between the dental implant and the periodontal membrane, indicating the deposition of the cementum including cementoblasts on the dental implant. Thus, the formation of an alveolar bone-periodontal membrane-dental root attachment system similar to the attachment system of an alveolar bone-periodontal membrane-dental root of a normal, natural tooth was found.

COMPARATIVE EXAMPLE 1

Preparation and experimentation of dental implant without bovine cementum particles immobilized thereon The same procedure was repeated as in Example 1, except that the crosslinked gelatin membrane described in Production Example 2 was used instead of the crosslinked gelatin membrane with bovine cementum particles immobilized therein described in Production Example 3.

The resultant periodontium formed around the dental implant in the specimens were observed with an optical microscope. As a result, dental ankylosis was found between the alveolar bone and the dental implant substantially throughout the interface therebetween.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A hybrid dental implant having cementum particles on a surface of a dental implant substrate, wherein the dental implant substrate is formed of at least one material selected from the group consisting of titanium, hydroxyapatite, silica, alumina, zirconia, and bioglass.

2. A hybrid dental implant according to claim 1, wherein a bioabsorbable membrane containing the cementum particles is formed on the dental implant substrate.

3. A hybrid dental implant according to claim 2, wherein the bioabsorbable membrane is made of at least one material selected from the group consisting of gelatin, crosslinked gelatin, collagen, and crosslinked collagen.

4. A hybrid dental implant according to claim 1, wherein the surface of the dental implant substrate is made of hydroxyapatite.

5. A hybrid dental implant according to claim 1, wherein the hybrid dental implant is sterilized with ethylene oxide gas.

6. A hybrid dental implant according to claim 1, wherein the hybrid dental implant is sterilized with electron beams.

7. A hybrid dental implant according to claim 1, wherein an average diameter of the cementum particles is between about 0.001 and about 0.1 mm.

8. A hybrid dental implant according to claim 1, wherein an average diameter of the cementum particles is between about 0.001 and about 0.075 mm.

9. A hybrid dental implant according to claim 1, wherein an amount of the cementum particle is between about 0.1 and about 6.0 mg/cm$^2$ of the surface of the dental implant substrate.

10. A hybrid dental implant according to claim 1, wherein an amount of the cementum particle is between about 0.5 and about 4.0 mg/cm$^2$ of the surface of the dental implant substrate.

11. A hybrid dental implant having cementum particles on a surface of a dental implant substrate, wherein an amount of the cementum particle is between about 0.1 and about 6.0 mg/cm$^2$ of the surface of the dental implant substrate.

12. A hybrid dental implant according to claim 11, wherein the amount of the cementum particle is between about 0.5 and about 4.0 mg/cm$^2$ of the surface of the dental implant substrate.

13. A hybrid dental implant according to claim 11, wherein the dental implant substrate is at least one material selected from the group consisting of titanium, hydroxyapatite, silica, alumina, zirconia, and bioglass.

14. A hybrid dental implant having cementum particles on a surface of a dental implant substrate, wherein an average diameter of the cementum particles is between about 0.001 and about 0.1 mm.

15. A hybrid dental implant according to claim 14, wherein the average diameter of the cementum particles is between about 0.001 and about 0.075 mm.

16. A hybrid dental implant according to claim 14, wherein the dental implant substrate is at least one material selected from the group consisting of titanium, hydroxyapatite, silica, alumina, zirconia, and bioglass.

* * * * *